US006730266B2

(12) United States Patent
Matson et al.

(10) Patent No.: US 6,730,266 B2
(45) Date of Patent: *May 4, 2004

(54) HEMOFILTRATION SYSTEMS, METHODS AND DEVICES USED TO TREAT INFLAMMATORY MEDIATOR RELATED DISEASE

(75) Inventors: James R. Matson, Dallas, TX (US); Patrice A. Lee, Erie, CO (US)

(73) Assignee: Immunocept, L.L.C., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/912,904

(22) Filed: Jul. 25, 2001

(65) Prior Publication Data

US 2001/0051106 A1 Dec. 13, 2001

Related U.S. Application Data

(63) Continuation-in-part of application No. 09/113,758, filed on Jul. 10, 1998, now Pat. No. 6,287,516.

(51) Int. Cl.[7] .................. A61M 1/36; A61M 37/00; B01D 9/00; B01D 37/00; C02F 9/00
(52) U.S. Cl. .................. 422/44; 604/4.01; 604/5.01; 604/5.04; 604/6.09; 604/6.11; 210/650; 210/195.2; 210/260; 210/790
(58) Field of Search .................. 604/4.01, 5.01–5.04, 604/6.01, 6.1, 6.09, 6.11, 252; 422/44, 261; 128/898; 210/348, 500.1, 645–46, 650–51, 767, 790–91, 195.1–195.2, 252, 257.2, 258–60, 288, 294–96, 416.1, 428, 433.1, 434, 660–61, 663, 669

(56) References Cited

U.S. PATENT DOCUMENTS 2,682,268 A 6/1954 Ryan .................. 604/252

4,000,072 A 12/1976 Sato et al. .................. 210/315
4,172,071 A 10/1979 De Maeyer et al. ........ 260/112

(List continued on next page.)

FOREIGN PATENT DOCUMENTS

| EP | 0 098 392 A2 | 6/1983 | .......... B01D/13/04 |
| EP | 0 787 500 A1 * | 8/1997 | |
| WO | 95/04559 | 2/1995 | ............ A61M/1/34 |

OTHER PUBLICATIONS

Konstanin et al. "Artificial Liver" from. Artificial Organs vol. 16 Issue pp. 235–242 Blackwell Publications Inc. Boston Ma 1992 International Society for Artificial Organs.
"Hemodiafiltration in Two Chambers Without Replacement Fluid: A Clinical Study" by C. Sanz–Moreno and J. Botella Artificial Organs vol. 19 No. 5 1995.
International Search Report for PCT/US/99/15426.
Seiichi Mochizuki et al.'s, "*Dextran transport through asymmetric ultrafiltration membranes: Comparison with hydrodynamic models*", Journal of Membrane Science, 68 (1992) pp. 21–41.
International Search Report PCT/US02/23603 5 pages.
International Search Report PCT/US03/07784 6 Pages.

*Primary Examiner*—Angela D. Sykes
*Assistant Examiner*—Patricia Bianco
(74) *Attorney, Agent, or Firm*—Baker Botts L.L.P.

(57) ABSTRACT

A hemofiltration system for a mammal is provided with a hemofilter and an adsorbent device. The hemofilter removes ultrafiltrate from a blood stream extracted from the mammal to create a filtered blood stream and an ultrafiltrate stream. The adsorbent device has one or more adsorbent materials and is used to adsorb inflammatory mediators from the ultrafiltrate stream received from the hemofilter removing inflammatory mediators that cause inflammatory mediator related disease, sepsis, and SIRS/MODS/MOSF to create a post adsorption ultrafiltrate stream. The post adsorption ultrafiltrate stream is selectively combined with the filtered blood stream and together with the filtered blood stream is returned to the mammal.

34 Claims, 6 Drawing Sheets

U.S. PATENT DOCUMENTS

| | | | |
|---|---|---|---|
| 4,248,736 A | 2/1981 | Fuchigami et al. | 252/428 |
| 4,313,831 A | 2/1982 | Lehmann et al. | 210/341 |
| 4,362,155 A | 12/1982 | Skurkovich | 128/214 |
| 4,402,940 A | 9/1983 | Nose et al. | 424/101 |
| 4,581,141 A | 4/1986 | Ash | 210/502 |
| 4,614,513 A | 9/1986 | Bensinger | 604/6 |
| 4,618,343 A | 10/1986 | Polaschegg | 604/29 |
| 4,787,974 A | 11/1988 | Ambrus et al. | 210/321.8 |
| 4,844,810 A * | 7/1989 | Richalley et al. | 210/321.72 |
| 4,872,983 A | 10/1989 | Dimantoglou et al. | 210/500 |
| 4,874,522 A | 10/1989 | Okamoto et al. | 210/645 |
| 4,897,189 A | 1/1990 | Greenwood et al. | 210/195 |
| 4,900,720 A | 2/1990 | Kotitschke | 514/21 |
| 5,211,850 A | 5/1993 | Shettigar et al. | 210/645 |
| 5,286,449 A | 2/1994 | Kuroda et al. | 422/48 |
| 5,450,516 A | 9/1995 | Pasquali et al. | 385/115 |
| 5,523,096 A | 6/1996 | Okarma et al. | 424/489 |
| 5,536,412 A | 7/1996 | Ash | 210/645 |
| 5,571,418 A * | 11/1996 | Lee et al. | 210/500.41 |
| 5,683,584 A | 11/1997 | Wenthold et al. | 210/500 |
| 5,744,042 A | 4/1998 | Stange et al. | 210/645 |
| 5,762,798 A | 6/1998 | Wenthold et al. | 210/500 |
| 5,851,394 A | 12/1998 | Shibata et al. | 210/500 |
| 5,855,782 A | 1/1999 | Falkenhagen et al. | 210/323.1 |
| 5,858,238 A | 1/1999 | McRea et al. | 210/645 |
| 5,919,369 A | 7/1999 | Ash | 210/645 |
| 5,919,444 A | 7/1999 | Norman, Jr. | 424/85.2 |
| 5,931,802 A | 8/1999 | Yoshida et al. | 604/4 |
| 5,945,337 A | 8/1999 | Brown | 435/389 |
| 6,008,199 A | 12/1999 | Grinnell et al. | 514/21 |
| 6,022,477 A | 2/2000 | Luo et al. | 210/645 |
| 6,039,946 A | 3/2000 | Strahilevitz | 424/140.1 |
| 6,042,784 A | 3/2000 | Wamsiedler et al. | 422/44 |
| 6,156,734 A | 12/2000 | Grinnell et al. | 512/21 |
| 6,193,681 B1 | 2/2001 | Davidner et al. | 604/6.08 |
| 6,287,516 B1 * | 9/2001 | Matson et al. | 210/650 |
| 6,497,675 B1 | 12/2002 | Davankov | 604/6.09 |

\* cited by examiner

HEMOFILTRATION SYSTEMS, METHODS AND DEVICES USED TO TREAT INFLAMMATORY MEDIATOR RELATED DISEASE

CROSS REFERENCE TO RELATED APPLICATIONS

This applicaton is a Continuation-in-Part Application of U.S. application Ser. No. 09/113,758 filed Jul. 10, 1998 entitled HEMOFILTRATION SYSTEMS, METHODS AND DEVICES USED TO TREAT INFLAMMATORY MEDIATOR RELATED DISEASE, now U.S. Pat. No. 6,287,516 issued Sep. 11, 2001.

This application is also co-pending with U.S. Application Ser. No. 09/815,675 filed Mar. 23, 2001, entitled METHOD AND SYSTEM FOR PROVIDING THERAPEUTIC AGENTS WITH HEMOFILTRATION FOR REDUCING INFLAMMATORY MEDIATOR RELATED DISEASES, and U.S. Application Ser. No. 09/858,210 filed May 15, 2001, entitled METHOD AND SYSTEM FOR COLLOID EXHANGE THERAPY.

TECHNICAL FIELD

The present invention relates generally to systems, methods, and devices used for hemofiltration. More specifically, the present invention relates to novel systems, methods, and devices for hemofiltration for inflammatory mediator-related diseases (IMRD), which include systemic inflammatory response syndrome ("SIRS"), multiorgan system dysfunction syndrome ("MODS"), and multiorgan system failure ("MOSF") (collectively "SIRS/MODS/MOSF").

BACKGROUND

Patients with life threatening illness are cared for in hospitals in the intensive care unit ("ICU"). These patients may be seriously injured from automobile accidents, etc., have had major surgery, have suffered a heart attack, or may be under treatment for serious infection, cancer, or other major disease. While medical care for these primary conditions is sophisticated and usually effective, a significant number of patients in the ICU will not die of their primary disease. Rather, a significant number of patients in the ICU die from a secondary complication known commonly as "sepsis" or "septic shock". Once again, the proper medical terms for sepsis and septic shock are systemic inflammatory response syndrome ("SIRS"), multiorgan system dysfunction syndrome ("MODS"), and multiorgan system failure ("MOSF") (collectively "SIRS/MODS/MOSF").

In short, medical illness, trauma, complication of surgery, and, for that matter, any human disease state, if sufficiently injurious to the patient, may elicit SIRS/MODS/MOSF. The systemic inflammatory response within certain physiologic limits is beneficial. As part of the immune system, the systemic inflammatory response promotes the removal of dead tissue, healing of injured tissue, detection and destruction of cancerous cells as they form, and mobilization of host defenses to resist or to combat infection. If the stimulus to the systemic inflammatory response is too potent, such as massive tissue injury or major microbial infection, however, then the systemic inflammatory response may cause symptoms which include fever, increased heart rate, and increased respiratory rate. This symptomatic response constitutes systemic inflammatory response syndrome ("SIRS"). If the inflammatory response is excessive, then injury or destruction to vital organ tissue may result in vital organ dysfunction, which is manifested in many ways, including a drop in blood pressure, deterioration in lung function, reduced kidney function, and other vital organ malfunction. This condition is known as multiorgan dysfunction syndrome ("MODS"). With very severe or life threatening injury or infection, the inflammatory response is extreme and can cause extensive tissue damage with vital organ damage and failure. These patients will usually die promptly without the use of ventilators to maintain lung ventilation, drugs to maintain blood pressure and strengthen the heart, and, in certain circumstances, artificial support for the liver, kidneys, coagulation, brain and other vital systems. This condition is known as multiorgan system failure syndrome ("MOSF"). These support measures partially compensate for damaged and failed organs, they do not cure the injury or infection or control the extreme inflammatory response which causes vital organ failures.

In the United States of America each year, SIRS/MODS/MOSF afflicts approximately 400,000–600,000 patients and results in about 150,000 deaths. Overall, depending on the number of organ systems failing, the mortality rate of MOSF ranges generally from 40 to 100%. For instance, if three (3) or more vital organs fail, death results in more the 90% of cases. SIRS/MODS/MOSF is the most common cause of death in intensive care units and is the thirteenth most common cause of death in the United States of America. SIRS/MODS/MOSF costs about $5 to $10 billion yearly for supportive care. In addition, the incidence of SIRS/MODS/MOSF is on the rise; reported cases increased about 139% between 1979 and 1987. This increase is due to an aging population, increased utilization of invasive medical procedures, immuno suppressive therapies (e.g. cancer chemotherapy) and transplantation procedures. (*Morbidity and Mortality Weekly Report* 1990; *Detailed Diagnoses and Procedures, National Hospital Discharge Survey*, 1993, from CDC/National Center for Health Statistics, October/95.)

The detrimental mechanism of SIRS/MODS/MOSF is the excessive activation of the inflammatory response. The inflammatory response consists of the interaction of various cell systems (e.g., monocyte/macrophage, neutrophil, and lymphocytes) and various humoral systems (e.g., cytokine, coagulation, complement, and kallikrein/kinin). Each component of each system may function as an effector (e.g., killing pathogens, destroying tissue, etc.), a signal (e.g., most cytokines), or both. Humoral elements of the inflammatory response were known as toxic mediators, but are now known collectively as inflammatory mediators ("IM"). IM include various cytokines (e.g., tumor necrosis factor ("TNF"); the interleukins; interferon, etc.), various prostaglandins (e.g., PG $I_2$, $E_2$, Leukotrienes), various clotting factors (e.g., platelet activating factor ("PAF")), various peptidases, reactive oxygen metabolites, and various poorly understood peptides which cause organ dysfunction (myocardial depressant factor ("MDF")). These compounds interact as a network with the characteristics of network preservation and self amplification. Some of these compounds, such as MDF and peptidases, are directly injurious to tissue; other compounds, such as cytokines, coordinate destructive inflammation. Infection (e.g., abscesses and sepsis) is a common complication of critical illness. Certain bacterial exotoxins, endotoxins or enterotoxins are extremely potent stimuli to SIRS/MODS/MOSF. Infection is the single most common cause of SIRS leading to MODS/MOSF. The development and use of effective antibiotics and other supportive measures have not had a significant effect on the death rate from MOSF.

The systemic inflammatory response with its network of systems (e.g., monocyte/macrophage, complement, antibody production, coagulation, kallikrein, neutrophil activation, etc.) is initiated and regulated through the cytokine ("CK") system and IM's. The CK system consists of more than thirty known molecules each of which activates or suppresses one or more components of the immune system and one or more CK in the network. The CK network is the dominant control system of the immune response. The sources of CK's are monocyte/macrophages and endothelial cells and they are produced in every tissue in the body. Key characteristics of the CK system are as follows: (i) CK are chemical signals coordinating immune system and associated system activities; (ii) commonly, two or more CK will trigger the same action providing a "fail safe" response to a wide variety of different stimuli (the systemic inflammatory response is critical to the individuals survival; these redundant control signals assure a system response which does not falter.); (iii) CK and IM concentrations (usually measured in blood) therefore increase in order to stimulate, control, and maintain the inflammatory response proportionally to the severity of the injury or infection; and (iv) as severity of injury or infection increases, the cytodestructive activity of the system increases resulting in MODS/MOSF. Therefore, high concentrations of CK and IM measured in the patient's blood, which are sustained over time, correlate with the patients risk of death.

Major research efforts by the biotechnology industry have sought cures for SIRS/MODS/MOSF, but none to date have been licensed by the United States Food and Drug Administration ("FDA") for use in humans. There is currently no definitive therapy for SIRS/MODS/MOSF (Dellinger, 1997; Natanson, 1994), even though a great deal of research funds have been spent on failed therapies for sepsis (Knaus, 1997). Critical care medicine techniques available to manage SIRS/MODS/MOSF are generally supportive in that they do not cure SIRS/MODS/MOSF. The biotechnology industry, however, has developed a number of prospective treatments for SIRS/MODS/MOSF. The general strategy of these prospective treatments is to identify what is conceived to be a key or pivotal single CK or IM. This single target CK or IM is then inactivated in an attempt to abate the inflammatory response. The most widely applied technologies used to inactivate CK or IM is binding with monoclonal antibodies ("MoAb") or specific antagonists ("SA"). MoAb's and SA's are used because they effectively bind the target CK or IM, or its receptor, usually in an "all or none" blockade. This strategy is problematic for two (2) reasons. First, the CK system is essential to mobilize the inflammatory response, and through it, the host immune response. If the CK system were blocked, death would ensue from unhealed injury or infection. Second, the CK and IM signals which make up the control network of the immune response consist of many redundant control loops to assure the "fail safe" initiation and continuation of this critical response. In the field of engineering, control theory indicates that a redundant, self amplifying system will not be effectively controlled by blocking one point, such as one CK or IM (Mohler, 1995).

Also, of interest, note the existing technique of hemofiltration ("HF"), which was developed as a technique to control over hydration and acute renal failure in unstable ICU patients. Existing HF techniques may use a hemofilter of some sort, which consists of a cellulose derivatives or synthetic membrane (e.g., polysulfone, polyamide, etc.) fabricated as either a parallel plate or hollow fiber filtering surface. Since the blood path to, through, and from the membrane is low resistance, the patients' own blood pressure drives blood through the filter circuit. In these HF applications, the hemofilter is part of a blood circuit. In passive flow HF, arterial blood flows through a large bore cannula, into plastic tubing leading to the filter; blood returns from the filter through plastic tubing to a vein. This is known as arteriovenous HF. Alternately, a blood pump is used, so that blood is pumped from either an artery or a vein to the filter and returned to a vein. This is known as pumped arterio-venous HF or pumped veno-venous HF. Ultrafiltrate collects in the filter jacket and is drained through the ultrafiltrate line and discarded. Ultrafiltrate flow rates are usually 250 ml–2000 ml/hour. In order to prevent lethal volume depletion, a physiologic and isotonic replacement fluid is infused into the patient concurrently with HF at a flow rate equal to or less than the ultrafiltrate flow rate. The balance of replacement fluid and ultrafiltrate is determined by the fluid status of the patient.

The pores of most filter membranes allow passage of molecules up to 30,000 Daltons with very few membranes allowing passage of molecules up to 50,000 Daltons. The membranes used to treat renal failure were generally designed to achieve the following specific goals: (i) to permit high conductance of the aqueous phase of blood plasma water needed to permit the formation of ultrafiltrate at a fairly low transmembrane pressure (typically 20–40 mm Hg), which requires a relatively large pore size that incidentally passes molecules of up to 30,000 to 50,000 Daltons; and (ii) to avoid passage of albumin (e.g., 68,000 Daltons). Note with these existing hemofilters used to treat renal failure, the ultrafiltrate contains electrolytes and small molecules (e.g., urea, creatinine, and uric acid), but no cells and only peptides and proteins smaller than the membrane pore size. The composition of the ultrafiltrate is very similar to plasma water. Loss of albumin, and subsequently, oncotic pressure, could cause or aggravate tissue edema and organ dysfunction (e.g., pulmonary edema), so hemofilters are designed to avoid this by having molecular weight exclusion limits well below the molecular weight of albumin (e.g., 68,000 Daltons).

During filtration of protein containing solutions, colloids or suspensions, or blood, the accumulation of protein as a gel or polarization layer occurs on the membrane surface. This gel layer typically reduces effective pore size, reducing the filterable molecular weights by roughly 10–40%. Therefore, pore sizes selected are somewhat larger than needed, anticipating a reduction in effective size. Thus, present membranes allow filtration and removal of excess water, electrolytes, small molecules and nitrogenous waste while avoiding any loss of albumin or larger proteins. These membranes are well-suited to their accepted uses, that is, treatment of over hydration and acute renal failure in unstable ICU patients.

Uncontrolled observations in ICU patients indicate that HF, in addition to controlling over hydration and acute renal failure, is associated with improvements in lung function and cardiovascular function. None of these improvements has been associated with shortened course of ventilator therapy, shortened ICU stay, or improved survival. The usual amount of ultrafiltrate taken in the treatment of over hydration and acute renal failure is 250 to 2000 ml/hour, 24 hours a day. A few published observations have suggested that higher amounts of ultrafiltrate brought about greater improvements in pulmonary and cardiovascular status; these have resulted in the development of a technique known as high volume HF ("HVHF"). In HVHF, from 2 to 9 liters/hour of ultrafiltrate are taken for periods of from 4 to 24 hours or more. Furthermore, preliminary uncontrolled or poorly controlled studies suggest that HVHF improves survival in patients with SIRS/MODS/MOSF; there is growing interest in the use of HVHF in SIRS/MODS/MOSF. There is however great hesitance to use HVHF for the following reasons: (i) the high volumes (currently 24–144 liters/day) of ultrafiltrate require equally high volumes of sterile, pharmaceutical grade replacement fluid; at these high volumes, errors in measuring ultrafiltrate coming out and replacement fluid flowing into the patient could cause injurious or lethal fluid overload or volume depletion; (ii) the high volume of ultrafiltrate removed could filter out of the blood desirable compounds from the patient resulting in dangerous deficiencies; this is currently theoretical, but should be taken seriously; (iii) large volumes of warm (body temperature) ultrafiltrate flowing out of the patient, and large volumes of cool (room temperature) replacement fluid flowing into the patient can cause thermal stress or hypothermia; and (iv) high volumes of replacement fluid add considerable expense to the therapy.

HVHF, as currently practiced, uses conventional hemofilters with pore sizes which provide a molecular weight cut of 30,000 Daltons and occasionally of 50,000 Daltons. The device and process described in U.S. Pat. No. 5,571,418 generally contemplates the use of large pore hemofiltration membranes with pore sizes to provide molecular weight exclusion limits of 100,000 to 150,000 Daltons. With these higher molecular weight cutoffs, these membranes are designed to remove a wider range of different IM's; these large pore membranes should remove excess amounts of all known IM's. These large pore hemofiltration membranes have been demonstrated in animal studies to be superior to conventional hemofilter membranes in improving survival time in a swine model of lethal *Staphylococcus aureus* infection (Lee, P A et al. *Critical Care Medicine* April 1998). It is anticipated that they will be superior to conventional membranes in SIRS/MODS/MOSF. However, it may be anticipated that in HVHF, the large pore membranes may also remove more different desirable compounds thus increasing the risk of the negative side effects of HVHF.

Other techniques used in the past to treat acute renal failure and/or SIRS/MODS/MOSF include hemodialysis and plasmapheresis. Hemodialysis is well suited to fluid and small solute (less the 10,000 Daltons) removal. However hemodialysis membranes remove very few IM (only those smaller than 5000 to 10,000 Daltons) and so have been ineffective in improving patient condition in SIRS/MODS/MOSF. In the unstable ICU patient, hemodialysis commonly results in rapid deterioration of cardiovascular function and pulmonary function requiring premature termination of the dialysis procedure. Hemodialysis has also been associated with increasing the occurrence of chronic renal failure in survivors of SIRS/MODS/MOSF. HF was specifically developed (Kramer, 1997) to avoid these complications of hemodialysis and has been very successful in doing so.

Plasmapheresis can be done with both membrane based and centrifugation based techniques. Plasmapheresis separates plasma and all that plasma contains from blood, leaving only formed elements. The removed plasma is usually replaced by either albumin solution or fresh frozen plasma. The removed plasma would contain all IM's. Studies of plasmapheresis in animal models of SIRS/MODS/MOSF have shown increased mortality with plasmapheresis compared to untreated control animals. No controlled study of plasmapheresis in humans with SIRS/MODS/MOSF has ever been done. The expense of albumin and fresh frozen plasma, and the risk of transmission of serious or deadly viral disease with fresh frozen plasma are serious drawbacks to the use of plasmapheresis in SIRS/MODS/MOSF.

Consequently, the prior art remains deficient in the lack of effective methods of treating IM related disease (e.g., SIRS/MODS/MOSF), which is safe. Furthermore, while high volume hemofiltration holds some promises, it is unworkable in its present form and is overly dangerous. The present invention fulfills this longstanding need and desire in this art.

SUMMARY

In accordance with teachings of the present disclosure, a system and method are described for hemofiltration for inflamatory mediator-related disease.

Preferred embodiments of the process and system treat inflammatory mediator-related disease, such as sepsis or SIRS/MODS/MOSF.

Specifically, preferred embodiments of the hemofiltration system are used in mammals. Preferred embodiments are generally comprised of a hemofilter, blood and ultrafiltrate lines, and an adsorptive device of one or more chambers containing adsorbent material of one or more types. The hemofilter receives a stream of blood removed from the mammal and removes ultrafiltrate from the stream of blood from the mammal and thereby creates a stream of filtered blood, which is eventually returned to the mammal, and a stream of ultrafiltrate. The hemofilter sieves the ultrafiltrate, the ultrafiltrate comprised of a fraction of plasma water, electrolytes, and peptides and small proteins. The sieved blood peptides and proteins have a molecular size smaller than the pore size of the membrane; IM are included in this group. The hemofilter is comprised of a biocompatible material. In particular, the hemofilter is comprised of a membrane and a jacket, wherein the membrane is selected from the group of biocompatible materials (e.g., polysulfone, polyacrylonitrile, polymethylmethacrylate, polyvinyl-alcohol, polyamide, polycarbonate, etc.) and cellulose derivatives, and the jacket is comprised of polycarbonate or some other suitable biocompatible material.

The adsorptive device is comprised of an encasement jacket. The adsorptive device incorporates one or more chambers containing adsorbent material of one or more types in the chamber or chambers. The adsorptive device receives the stream of ultrafiltrate and selectively or nonselectively removes IM that cause inflammatory mediator-related disease, such as sepsis and SIRS/MODS/MOSF, from the ultrafiltrate removed from the blood of the mammal to create a stream of post adsorption ultrafiltrate. The adsorptive device is preferably comprised of an encasement jacket comprised of polycarbonate or other suitable biocompatible material and may be configured as having one or more chambers. Each chamber may contain an adsorbent material or a combination of adsorbent materials. The adsorptive device is designed to be placed in the line transferring ultrafiltrate removed by the hemofilter and adsorbs IM from the ultrafiltrate producing "post adsorption ultrafiltrate." The stream of post adsorption ultrafiltrate is eventually combined or reinfused, in whole or in part, with the stream of filtered blood and returned to the mammal. The adsorbent material may be comprised of a host of materials, including, but not limited to, activated charcoal, uncharged resins, charged resins, silica, immobilized polymyxin B, anion exchange resin, cation exchange resin, neutral exchange resin, polysulfone, polyacrylonitrile, polymethylmethacrylate, polyvinyl-alcohol, polyamide, polycarbonate, cellulose derivatives, immobilized monoclonal antibodies, immobilized IM receptors, and immobilized specific antagonists. The adsorbent material may also be organized in a number of ways, including a matrix of rods, a porous sieve, a matrix of porous material which conveniently presents adsorbent materials to ultrafiltrate, and beads. Each adsorbent material may be uncoated or coated; the adsorbent material and/or the adsorbent device should prevent or contain dissolution and fragmentation of adsorbent material.

In addition, preferred embodiments may also be comprised of a blood pump to pump the blood from the mammal, an ultrafiltrate waste pump to pump a portion of the ultrafiltrate to the waste reservoir, an ultrafiltrate return pump to pump ultrafiltrate back into the blood circuit returning the ultrafiltrate to the patient, a three-way stop cock or a first three-way joint, and a second three-way joint. First tubing transfers the blood from the mammal to the blood pump; second tubing transfers the blood from the blood pump to hemofilter; third tubing transfers the filtered blood filtered by the hemofilter to the three-way joint or three-way stop cock; fourth tubing transfers the filtered blood along with the post adsorption ultrafiltrate to the mammal; fifth tubing transfers the ultrafiltrate to the adsorptive device; sixth tubing transfers the post adsorption ultrafiltrate to second three-way joint; seventh tubing transfers post adsorption ultrafiltrate to the first ultrafiltrate return pump; eighth tubing transfers post adsorption ultrafiltrate from the first ultrafiltrate return pump to three-way joint or three-way stop cock joining fourth tubing which transfers filtered blood along with the post adsorption ultrafiltrate to the mammal; ninth tubing transfers post adsorption ultrafiltrate to second ultrafiltrate waste pump; and tenth tubing transfers post adsorption ultrafiltrate from second ultra filtrate waste pump to waste reservoir. Note that there are alternate embodiments.

Finally, alternative preferred embodiments may utilize a single filter, which would be a "two-stage" filter, that incorporates both the hemofilter and the adsorptive device containing the adsorbent materials(s). Note for the purpose of discarding a portion of ultrafiltrate, a second ultrafiltrate pump can be used along with associated changes to the necessary tubing.

Preferred processes to treat IM related diseases and SIRS/MODS/MOSF in a mammal are comprised of the following steps: (a) removing blood from the mammal to create a blood stream; (b) filtering the blood stream to remove ultrafiltrate from the blood to create an ultrafiltrate stream and a filtered blood stream; (c) circulating the ultrafiltrate stream to the adsorptive device to remove IM that cause IM related disease and SIRS/MODS/MOSF to create a post adsorption ultrafiltrate stream; (d) combining the post adsorption ultrafiltrate stream with the filtered blood stream to create a post adsorption ultrafiltrate/filtered blood stream; and (e) returning the post adsorption ultrafiltrate/filtered blood stream to the mammal. Additional steps may include after step (a), (a1) pumping the blood stream; and after step (b), (b1) circulating ultrafiltrate to the ultrafiltrate waste pump and on to the waste reservoir and after step (c), (c1) pumping the post adsorption ultrafiltrate stream circulating the post adsorption ultrafiltrate stream to the post hemofilter blood line, or alternatively, to any convenient tubing or vascular canula which returns post adsorption ultrafiltrate stream to the mammal's vascular system.

Preferred embodiments provide a number of advantages, important functions and key features. In particular, the use of preferred embodiments allows the safe use of two stage high volume hemofiltration ("HVHF") with its improved patient survival, avoids dangerous fluid balance errors inherent to conventional HVHF, avoids the risk of depletion of desirable humoral compounds, avoids or minimizes thermal stress and hypothermia, and avoids the cost of excessive amounts of replacement fluid. The immune system has many, redundant CK and IM control loops; several of these loops must be down regulated if system wide control is to be achieved and death from SIRS/MODS/MOSF prevented. The preferred embodiments address this task.

Moreover, the use of the adsorptive device comprised of adsorbent material(s) provides additional advantages. Conventional hemofiltration (i.e., hemofiltration performed to treat acute renal failure) usually requires the production of and discard of from about 200 ml to 2,000 ml of ultra filtrate per hour. In patients, if this volume were not replaced, the loss of fluid would soon lead to dehydration, shock and death. In practice, some or all of this hourly loss is replaced each hour as either medicinal or nutrient solutions, or, in whole or in part, with an isotonic, physiologic, sterile, pharmaceutical grade intravenous solution known as replacement fluid. The pumps used to control ultrafiltrate and replacement fluid flow are either intravenous fluid pumps or roller pumps adapted for this purpose. These pumps can have an error of from 5–10% and still be considered acceptable for clinical purposes. Bedside nurses monitor actual fluid balance and correct errors. For conventional hemofiltration, these devices and techniques do not usually introduce serious errors, partly due to the level of fluid extracted, filtered, and replaced. However, various investigators have adapted hemofiltration for use in SIRS/MODS/MOSF by markedly increasing the volume of ultrafiltrate taken each hour. As discussed above, this technique is known as HVHF and requires that from 2 to 9 liters/hour of ultrafiltrate be taken from the patient. Small, uncontrolled studies with HVHF suggest that HVHF can significantly improve vital organ function, shorten the duration of vital organ failure, and improve patient survival in SIRS/MODS/MOSF.

Criticisms of HVHF include: (i) the risk of fluid balance errors with high fluid flux; (ii) the risk of depletion of desirable compounds; (iii) the risk of hypothermia; and (iv) expense. First, with respect to the risk of high fluid flux, the high volumes of ultrafiltrate (about 48 to 150 liters/day) and replacement fluid (about 48 to 150 liters/day), being pumped on current equipment, could result in large and dangerous fluid imbalances. With current equipment, imbalances of as much as 30 liters of excess fluid delivered to the patient, or 30 liters of excess fluid removed from the patient could occur. Any error approaching this magnitude in either direction would be very injurious or lethal to the patient. Hence, HVHF is considered by many to be dangerous and potentially deadly. Second, with respect to the risk of depletion of desirable compounds, the high volumes of ultrafiltrate (about 48 to 150 liters/day) removed from the patient do remove large amounts of IM with resulting improvements in SIRS/MODS/MOSF. However, these high volumes may also remove desirable compounds with deleterious effects. This criticism is theoretical at this time but should be taken seriously. Third, with respect to the risk of hypothermia, about 48 to 150 liters of warm (body temperature) ultrafiltrate are removed from the patient causing heat loss, and about 48 to 150 liters of cool (room temperature) replacement fluid is infused into the patient causing cooling. This flux causes thermal stress and may cause hypothermia. Thermal stress creates additional energy demands on these already critically stressed patients and may compromise there condition. Fourth, with respect to the expense, the high volumes of ultrafiltrate (about 48 to 150 liters/day) require equal or nearly equal volumes of isotonic, physiologic, sterile, pyrogen free, pharmaceutical grade replacement fluid (RF). Such fluid is expensive and in these large quantities would add substantially to the cost of patient care.

As stated above, the use of the adsorbent device by preferred embodiments addresses these concerns. First, with respect to the risk of high fluid flux, the adsorbent device adsorbs IM from the ultrafiltrate thus removing them from the ultrafiltrate; the post adsorption ultrafiltrate may then be reinfused, in whole or in part, back into the patient. Since post adsorption ultrafiltrate is returned to the patient, in whole or in part, the amount of replacement fluid needed to preserve fluid balance in the patient is sharply reduced (to the amount of ultrafiltrate discarded), or eliminated entirely. The volumes of ultrafiltrate discarded and replacement fluid infused will need to be only those indicated by the patients state of edema (over hydration) and/or needs to accommodate medicinal or nutrient solutions; typically 2 to 6 liters per day. These lower volumes of fluid flux (about 2 to 6 liters per day) can be safely managed by existing pump technology, pumping errors on these small volumes are well tolerated. Second, with respect to the risk of depletion of desirable compounds, as all or most of the ultrafiltrate will be returned to the patient (as post adsorption ultrafiltrate), and as adsorbent material will be selected with as narrow a range of adsorbed substances as possible and focused on IM, the loss of desirable substances is minimized. Third, with respect to the risk of hypothermia, as warm (body temperature) ultrafiltrate is returned to the patient, the amount of cool (room temperature) replacement fluid needed will be sharply reduced. This will eliminate the heat loss which would otherwise occur with discard of ultrafiltrate and also eliminate the cooling which would occur by the infusion of cool replacement fluid. In this way, the stress of hypothermia is eliminated. Fourth, with respect to the expense, the cost of RF varies widely depending on markets, contract arrangements and other considerations. However, $2 to $10 per liter are typical costs. Thus, HVHF could create an incremental cost of from $96 to $1,500 per day. By reinfusion of post adsorption ultrafiltrate following adsorption of IM's, and so eliminating the need for all or most replacement fluid, this incremental cost is eliminated. In summary, HVHF is a technique which may significantly improve survival in SIRS/MODS/MOSF, however, HVHF creates new and substantial risks and expenses. Preferred embodiments eliminate or sharply reduce these risks and expenses, and make HVHF much safer and more cost effective in patients suffering from SIRS/MODS/MOSF.

Other advantages of the invention and/or inventions described herein will be explained in greater detail below.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

The accompanying drawings are incorporated into and form a part of the specification to illustrate several examples of the present inventions. These drawings together with the description serve to explain the principles of the inventions. The drawings are only for the purpose of illustrating preferred and alternative examples of how the inventions can be made and used and are not to be construed as limiting the inventions to only the illustrated and described examples. Further features and advantages will become apparent from the following and more particular description of the various embodiments of the invention, as illustrated in the accompanying drawings, wherein.

DETAILED DESCRIPTION

Figure 1A:
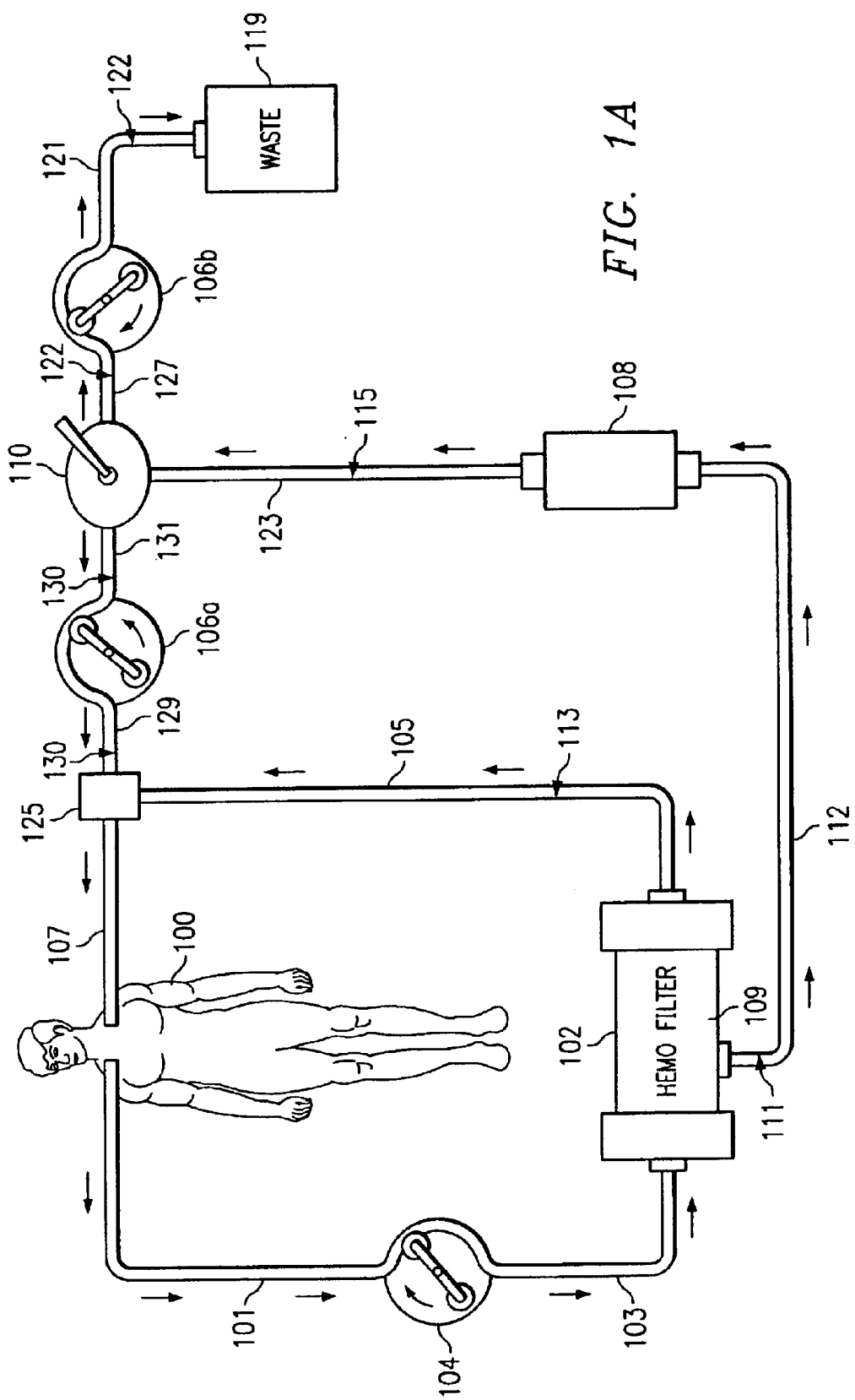
FIG. 1A is a schematic of the physical layout of various components of a preferred embodiment, including mammal 100, hemofilter 102, blood pump 104, first ultra-filtrate pump 106a and second ultrafiltrate pump 106b, adsorptive device 108 having one or more chambers containing adsorbent material of one or more types, three-way stop cock or first three-way joint 110, second three-way joint 125, and associated tubing.

The preferred embodiment will be described by referring to apparatus showing various examples of how the inventions can be made and used. When possible, like reference characters are used throughout the several views of the drawing to indicate like or corresponding parts.

Related Definitions

As a point of reference, please note the following terms and definitions.

The term "hemofiltration" refers to a process of filtering blood by a membrane with separation of all formed elements, all proteins larger than effective pore size of the membrane, and retained plasma water and solute (these return to the patient) from ultrafiltrate.

The term "ultrafiltrate" refers to the filtered plasma water and solute and molecules (including target peptides and proteins containing IM) smaller than effective pore size of the membrane. The term "Systemic Inflammatory Response Syndrome" ("SIRS") refers to the excessive and dysfunctional elaboration by a human patient of inflammatory mediators ("IM") which results in an excessive and injurious inflammatory response.

The term "Multiple Organ Dysfunction Syndrome" ("MODS") refers to SIRS causing injury or destruction to vital organ tissue and resulting in vital organ dysfunction, which is manifested in many ways, including a drop in blood pressure, deterioration in lung function, reduced kidney function, and other vital organ malfunction.

The term "Multiple Organ System Failure" ("MOSF") refers to the clinical syndrome of vital organ dysfunction or failure due to tissue injury resulting from SIRS. Its mortality rate is approximately 40–100%.

The term "Inflammatory Mediator Related Disease" ("IMRD") refers to any disease state characterized by injurious or lethal excess production of IM. Diseases commonly included in this category include Lupus Erythematosus, Hemolytic Uremic Syndrome, Bullous Pemphigoid, pemphigus vulgaris, sepsis, SIRS/MODS/MOSF, and the like.

The term "Inflammatory Mediators" or "IM" refers to a heterogeneous group of chemicals synthesized and released by human tissue. IM include cytokines, prostaglandins, oxygen metabolites, kinins, complement factors, various clotting factors, various peptidases, various peptides, various proteins, and various toxic peptides. The molecular weight range of known IM is 1,000–100,000 Daltons.

The term "Hemofilter" refers to the filter used in hemofiltration. It can be configured in a number of ways, such as a series of parallel plates or as a bundle of hollow fibers. The blood path is from a blood inlet port, through the fibers or between the plates, then to a blood outlet port. Filtration of blood occurs at the membrane with ultrafiltrate forming on the side of the membrane opposite the blood. This ultrafiltrate accumulates inside the body of the filter contained and embodied by the filter jacket. This jacket has an ultrafiltrate drainage port.

The term "large pore hemofiltration" refers to the use of a membrane or other types of filtration media which may remove albumin from a patient's blood stream. For some applications, a large pore hemofilter may have molecular weight exclusion limits equal to or greater than approximately 69,000 Daltons to treat SIRS, MODS, MOSF and IMRD in accordance with teachings of the present invention. For some applications large pore hemofiltration, performed in accordance with teachings of the present invention, may permit removal of more albumin from a patient's blood stream than some previous hemofiltration techniques. However, teachings of the present invention substantially reduce or eliminate negative effects from removing increased amounts of albumin or other desirable compounds from a patient's blood stream during large pore hemofiltration. The term "large pore hemofilter" refers to a hemofilter satisfactory for use in providing large pore hemofiltration in accordance with teachings of the present invention.

Figure 1B:
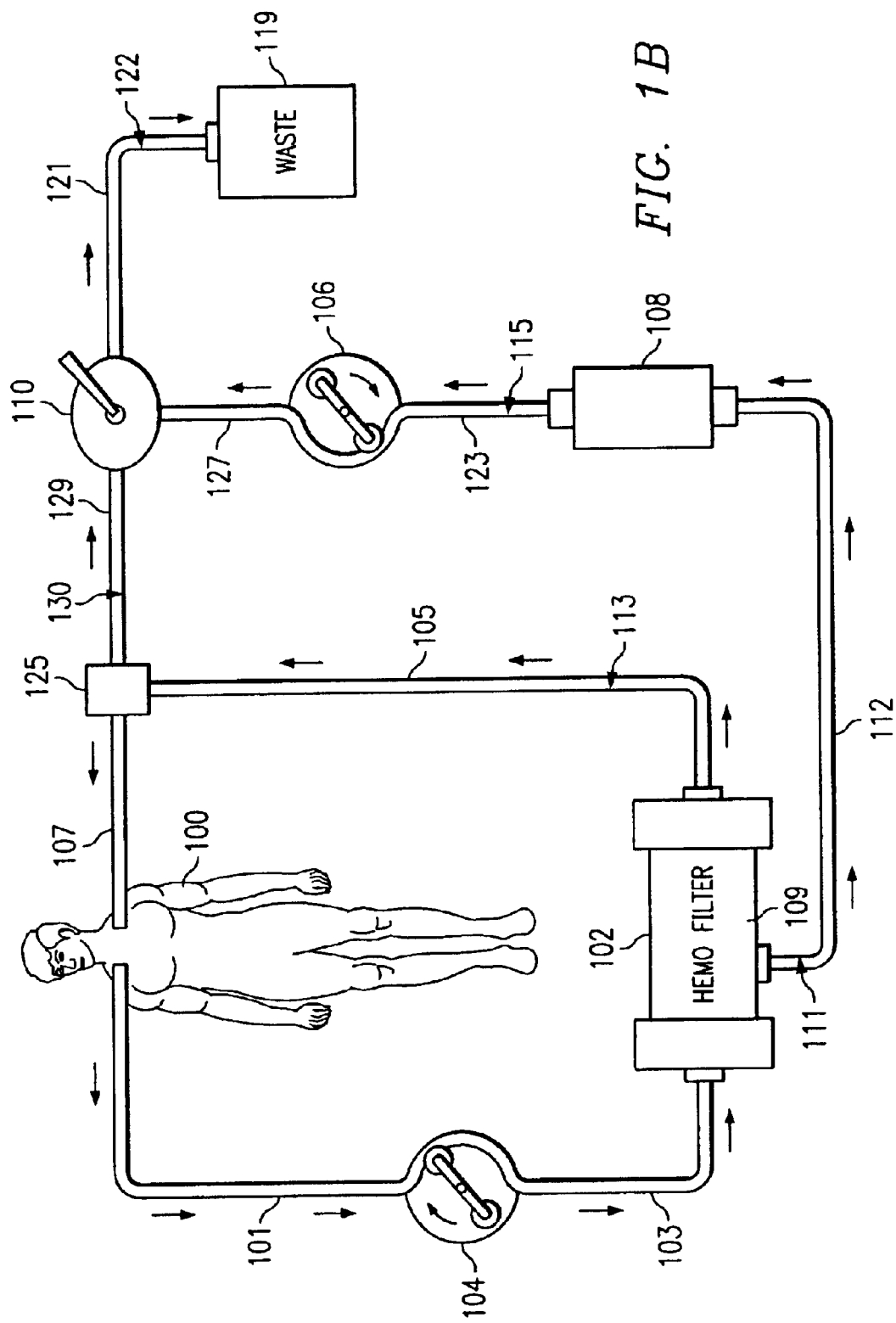
FIG. 1B is a schematic of the physical layout of various components of a preferred embodiment, including mammal 100, hemofilter 102, blood pump 104, single ultra-filtrate pump 106, adsorptive device 108 having one or more chambers containing adsorbent material of one or more types, three-way stop cock or first three-way joint 110, second three-way joint 125, and associated tubing.
Figure 2:
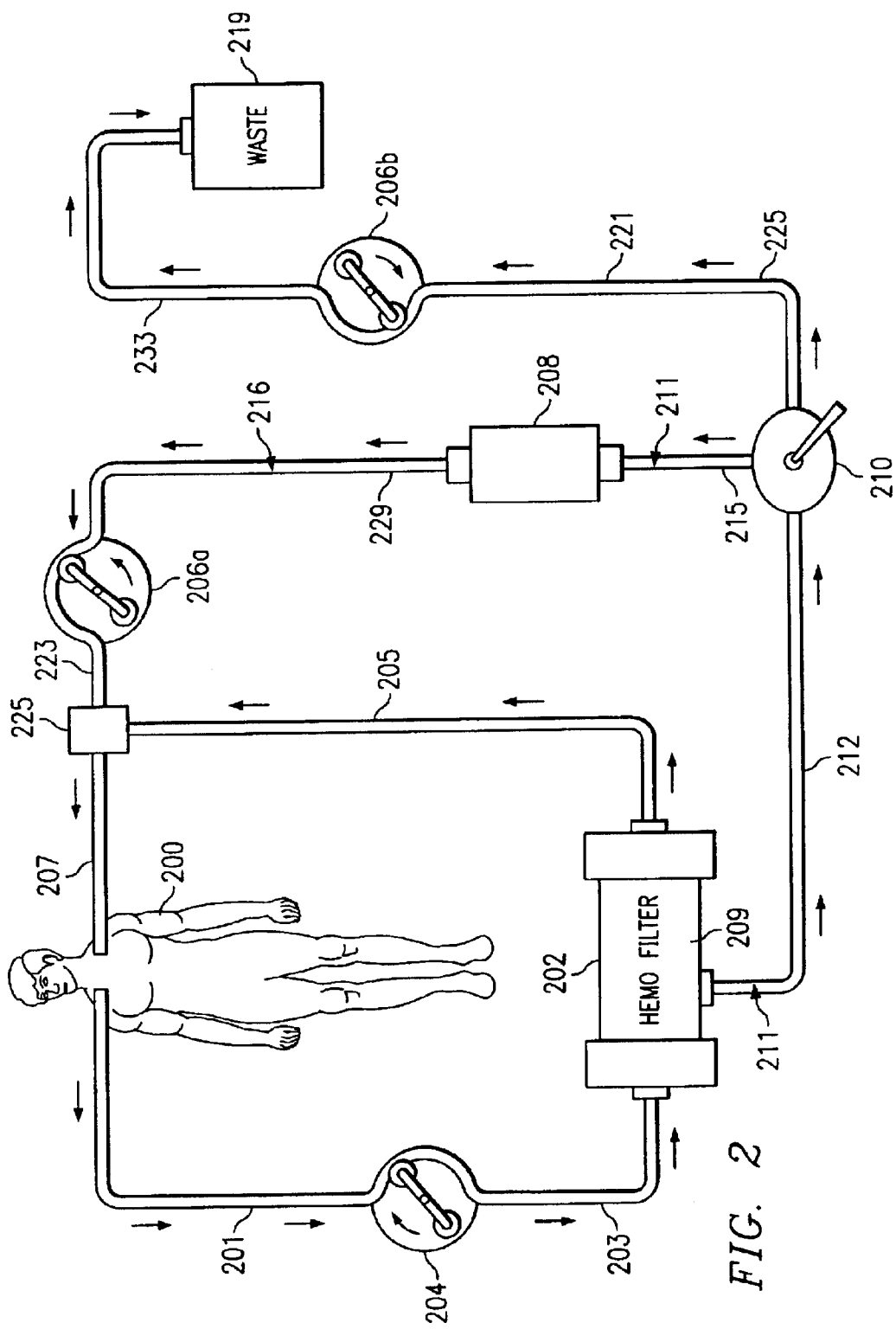
FIG. 2 is a schematic of an alternate physical layout of various components of a preferred embodiment, including mammal 200, hemofilter 202, blood pump 204, first ultrafiltrate pump 206a and second ultra-filtrate pump 206b, adsorptive device 208 having one or more chambers containing adsorbent material of one or more types, three-way stop cock or first three-way joint 210, second three-way joint 225, and associated tubing.
Figure 3A:
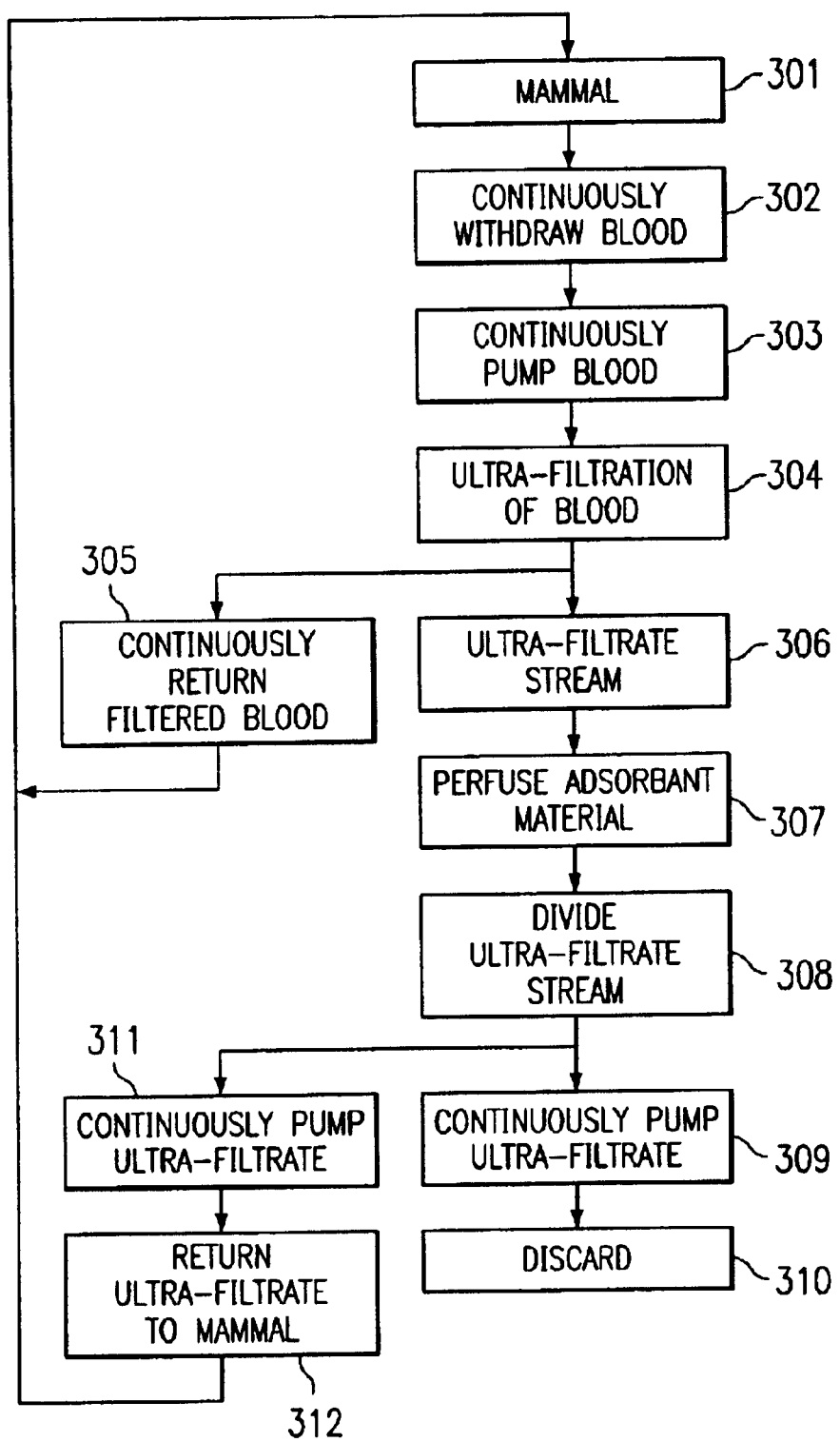
FIG. 3A is a diagram showing the system flow of a preferred embodiment shown in FIG. 1A.
Figure 3B:
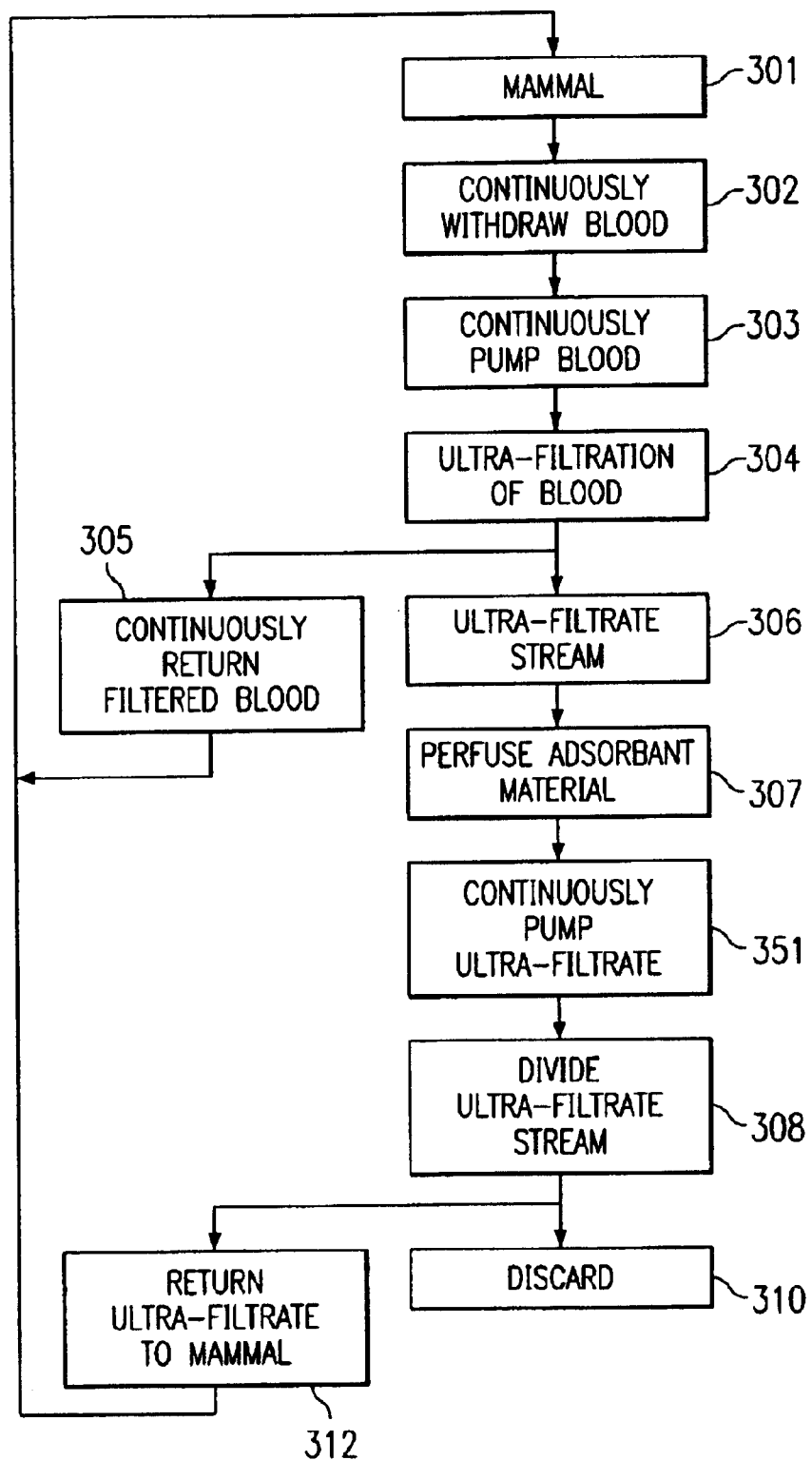
FIG. 3B is a diagram showing the system flow of a preferred embodiment shown in FIG. 1B.
Figure 4:
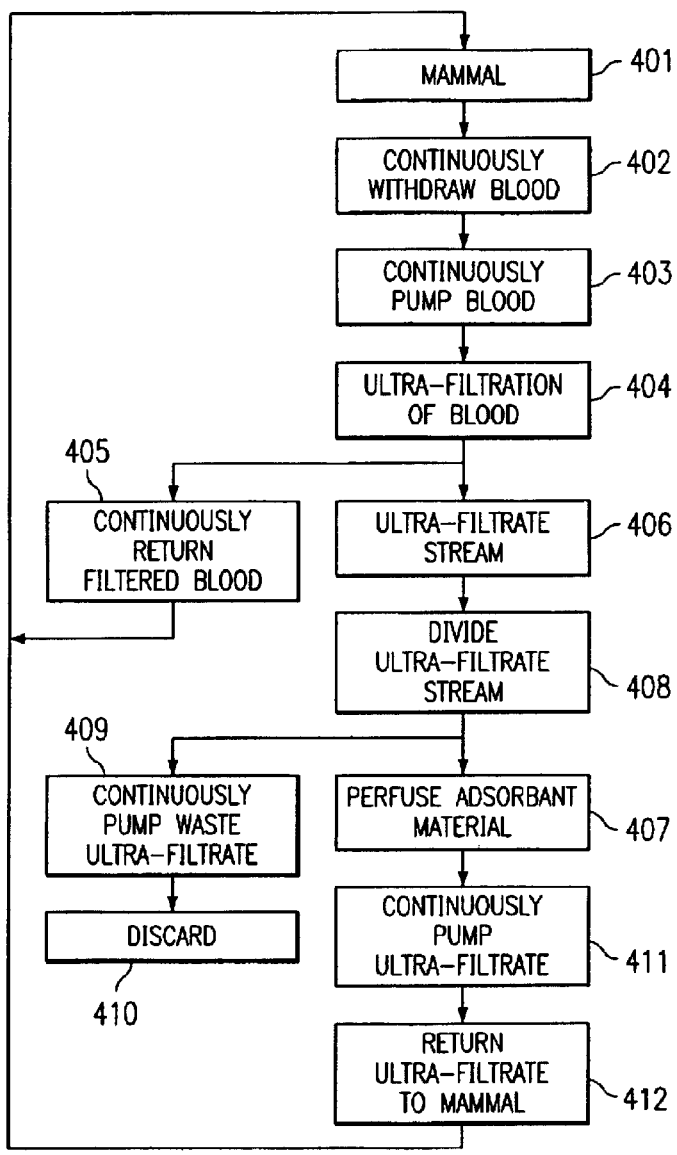
FIG. 4 is a diagram showing the system flow of a preferred embodiment shown in FIG. 2.

FIG. 1A is a schematic of the physical layout of various components of a preferred embodiment, including mammal 100, hemofilter 102, blood pump 104, first ultrafiltrate pump 106a, second ultrafiltrate pump 106b, adsorptive device 108 having one or more chambers containing adsorbent material of one or more types, three-way stop cock or first three-way joint 110, second three-way joint 125, and associated tubing. FIG. 1B is similar to FIG. 1A, except that single ultrafiltrate pump 106 is used in lieu of first ultrafiltrate pump 106a and second ultrafiltrate pump 106b. Both FIGS. 1A and 1B position three-way stop cock or first three-way joint 110 in such a manner that it divides ultrafiltrate stream downstream from adsorptive device 108. FIG. 2 is an alternate schematic of the physical layout of various components of a preferred embodiment shown in FIGS. 1A and 1B, except that three-way stop cock or first three-way joint 210 divides ultrafiltrate stream before adsorptive device 208. FIGS. 3A and 3B are diagrams showing the system flow of a preferred embodiment shown in FIGS. 1A and 1B, respectively. FIG. 4 is a diagram showing the system flow of a preferred embodiment shown in FIG. 2.

Steps 301 and 302 (in FIGS. 3A and 3B) and steps 401 and 402 (in FIG. 4) show blood being continuously withdrawn from mammal 100 (in FIGS. 1A and 1B) and mammal 200 (in FIG. 2) and directed to blood pump 104 (in FIGS. 1A and 1B) and blood pump 204 (in FIG. 2) via first tubing 101 (in FIGS. 1A and 1B) and first tubing 201 (in FIG. 2). Specifically, step 303 (in FIGS. 3A and 3B) and step 403 (in FIG. 4) show the continuous pumping of blood by blood pump 104 into hemofilter 102 via second tubing 103 (in FIGS. 1A and 1B) and by blood pump 204 into hemofilter 202 via second tubing 203 (in FIG. 2). Mammal 100 (in FIGS. 1A and 1B) and mammal 200 (in FIG. 2), such as a human being, preferably have a major blood vessel cannulated allowing for the continuous withdrawal of blood by blood pump 104 (in FIGS. 1A and 1B) and blood pump 204 (in FIG. 2). As shown in steps 304 and 306 (in FIGS. 3A and 3B) and steps 404 and 406 (in FIG. 4), hemofilter 102 ultra-filtrates blood extracted from mammal 100 (in FIGS. 1A and 1B) and hemofilter 202 ultra-filtrates blood extracted from mammal 200 (in FIG. 2). And, step 305 (in FIGS. 3A and 3B) and step 405 (in FIG. 4) returns blood filtered by hemofilter 102 to mammal 100 via third tubing 105 and fourth tubing 107 in FIGS. 1A and 1B and by hemofilter 202 to mammal 200 via third tubing 205 and fourth tubing 207 in FIG. 2.

Referring to FIGS. 1A, 1B, and 2, ultrafiltration is a filtration process in which blood cells and blood proteins with a molecular size larger than the pore size of hemofilter membrane 109 (in FIGS. 1A and 1B) and hemofilter membrane 209 (in FIG. 2) are tamed in the blood path. The composition of hemofilter membrane 109 (in FIGS. 1A and 1B) and hemofilter membrane 209 (in FIG. 2) are preferably comprised of biocompatible material, such as polysulfone, polyacrylonitrile, polymethylinethacrylate, polyvinyl-alcohol, polyamide, polycarbonate, cellulose derivatives, etc., but is not limited to these materials. The jacket of the hemofilter will be preferably comprised of a biocompatible material, such as polycarbonate, but not limited to, polycarbonate. Hemofilter membrane 109 (in FIGS. 1A and 1B) and hemofilter membrane 209 (in FIG. 2) are preferably organized as a parallel plate membrane or as a membrane hollow fiber. Hemo filter membrane 109 in FIGS. 1A and 1B and hemofilter membrane 209 in FIG. 2 are preferably comprised of large pore hemofiltration membranes, which are preferably fabricated from any biocompatible material suitable for the purpose such as polysulfone, polyacrylonitrile, polymethylmethacrylate, polyvinyl-alcohol, polyamide, polycarbonate, cellulose derivatives, etc., but, of course, without limitation to these materials.

As shown in step 304 in FIGS. 3A and 3B, hemofilter membrane 109 (in FIGS. 1A and 1B) sieves a fraction of plasma water, electrolytes, blood peptides and proteins with a molecular size smaller than the pore size of the membrane to form ultrafiltrate stream 111 (in FIGS. 1A and 1B), which is directed to adsorptive device 108 (in FIGS. 1A and 1B), which has one or more chambers containing adsorbent material of one or more types, via fifth tubing 112 (in FIGS. 1A and 1B). As shown in step 307 in FIGS. 3A and 3B, adsorptive device 108 is perfused by ultrafiltrate stream 111. Similarly, as shown in step 404 in FIG. 4, hemofilter membrane 209 (in FIG. 2) sieves a fraction of plasma water, electrolytes, blood peptides and proteins with a molecular size smaller than the pore size of the membrane to form ultrafiltrate stream 211 (in FIG. 2), which is directed to adsorptive device 208 (in FIG. 2), which has one or more chambers containing adsorbent material of one or more types, via fifth tubing 212, and sixth tubing 215 (in FIG. 2).

As shown in step 407 in FIG. 4, adsorptive device 208 is perfused by ultrafiltrate stream 211.

As shown in steps 308 in FIGS. 3A and 3B, ultrafiltrate stream 115 (in FIGS. 1A and 1B) is divided at three-way stop cock or first three-way joint 110 (in FIGS. 1A and 1B), after adsorptive device 108 in FIGS. 1A and 1B. As shown by step 408 in FIG. 4, ultrafiltrate stream 211 (in FIG. 2) is divided at three-way stop cock or first three-way joint 210 (in FIG. 2), before adsorptive device 208 in FIG. 2.

Specifically, in FIG. 1A, after three-way stop cock or first three-way joint 110 divides post-adsorptive ultrafiltrate stream 115, discard ultrafiltrate stream 122 is directed toward second ultra-filtrate pump 106b and to waste reservoir 119 and return ultrafiltrate stream 130 is directed toward first ultra-filtrate pump 106a and on to mammal 100. In FIG. 1B, ultrafiltrate stream 115 is directed toward single ultrafiltrate pump 106 and discard ultrafiltrate stream 122 is directed to waste reservoir 119 and return ultrafiltrate stream 130 is returned to mammal 100. In FIG. 2, ultrafiltrate stream 211 is directed toward three-way stop cock 210 and discard ultrafiltrate stream 221 is directed toward second ultrafiltrate pump 206b and then onto waste reservoir 219 and return ultrafiltrate stream 216 is directed toward first ultrafiltrate pump 206a and eventually returned to mammal 200.

Figure 5A:
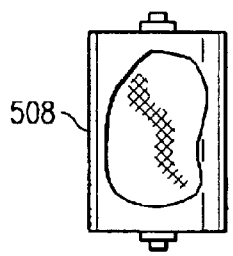
FIGS. 5A, 5B, and 5C are diagrams showing alternate preferred embodiments of adsorbent device 108 (in FIGS. 1A and 1B) and adsorptive device 208 (in FIG. 2).
Figure 5B:
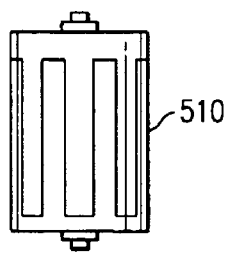
Figure 5C:
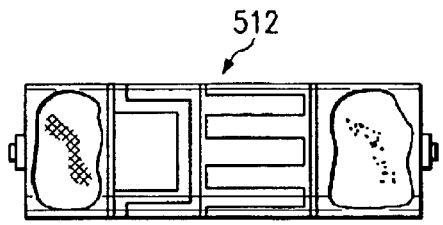

Adsorptive device 108 (in FIGS. 1A and 1B) and adsorptive device 208 (in FIG. 2) have one or more chambers containing adsorbent materials(s). The adsorbent material(s) is (are) preferably fixed or contained within the respective adsorbent device and none will pass into the ultrafiltrate stream or return to mammal 100 (in FIGS. 1A and 1B) and mammal 200 (in FIG. 2). The adsorbent materials used in the preferred embodiment may be coated or uncoated. The nature of the adsorbent materials used in the preferred embodiment is such that solutes to be adsorbed will be bound to the adsorbent materials. As shown in FIGS. 5A, 5B, and 5C, adsorbent material is presented to ultrafiltrate flow by structures such as rods or plates, or flows through structures such as beads or porous matrix of any configuration effective in presentation of adsorptive material(s) to ultrafiltrate stream, or flows through one or more chambers containing immobilized particulate, beaded or fragmented adsorbent material. Adsorbent materials may include, but are not limited to: silica, activated charcoal, nonionic resins, ionic resins, immobilized polymyxin B, anion exchange resin, cation exchange resin, neutral exchange resin, immobilized monoclonal antibodies, immobilized IM receptors, immobilized specific antagonists, cellulose and its derivatives, synthetic materials (e.g., polysulfone, polyacrylonitrile, polymethylmethacrylate, polyvinyl-alcohol, polyamide, polycarbonate, etc.) and the like or any combination thereof. The selection of adsorbent materials depends on the inflammatory mediators to be removed. Preferred embodiment uses polymyxin to remove endotoxin, anti-TNF antibody to remove TNF, polyacrylonitrile to remove interleukin 1-beta and TNF, among other adsorbents, both specific and nonspecific. Adsorbents may also be used in various combinations as the patients condition and stage of disease warrant.

FIGS. 5A, 5B, and 5C are diagrams showing preferred embodiments of adsorptive device 108 (in FIGS. 1A and 1B) and adsorptive device 208 (in FIG. 2), both of which have one or more chambers containing adsorbent material of one or more types. Adsorbent materials vary widely in their adsorptive capacity, and types and conditions of substances adsorbed. IM are of many different chemical types (e.g. peptides, lipids) and each IM's charge and plasma binding (e.g., specific or nonspecific circulating soluble receptors) will vary the characteristics of how they may be adsorbed during the course of any inflammatory mediator related disease ("IMRD") or episode of SIRS/MODS/MOSF. For this reason, various adsorbent materials will be used in order to provide the range of chemical binding characteristics and capacity needed for removal of many IM from ultrafiltrate. As stated above, adsorbent materials are of different chemical and physical types. Particulate adsorbent materials (e.g. charcoal; beads of polysulfone, polyacrylonitrile, polymethylmethacrylate, polyvinyl-alcohol, polyamide, polycarbonate, cellulose derivatives, and similar materials; liposomes, etc.) may be coated or uncoated, but are usually encased in a porous flexible mesh sac or rigid porous containment jacket which allows free access of perfusing fluid (e.g. ultrafiltrate) but contains the particles and prevents them from being carried back to the mammal in the ultrafiltrate stream. Some adsorbents (e.g. silica gel) lend themselves to being cast or otherwise fabricated in various rigid or semirigid configurations (e.g. rods, plates etc.) which allow for effective and convenient presentation of ultrafiltrate containing IM to the adsorbent material. Some adsorbents (e.g. monoclonal antibodies, IM receptors, specific antagonists, polymyxin B) will need to be affixed to a supporting matrix of biocompatible material (e.g. polycarbonate and the like) for presentation of adsorbent material to the ultrafiltrate stream containing IM. The matrix of biocompatible material will be configured to allow effective and convenient presentation of ultrafiltrate containing IM to the affixed adsorbent material.

Depending on physical and chemical compatibilities of the adsorbent materials, and the requirements of adequate ultrafiltrate flow, adsorbent device 108 (in FIGS. 1A and 1B) and adsorbent device 208 (in FIG. 2) may be configured as one chamber containing one or more adsorbent materials, as shown in adsorptive device 508 in FIG. 5A and adsorptive device 510 in FIG. 5B, or separated into multiple chambers each containing one or more adsorbent materials, as shown in adsorptive device 512 in FIG. 5C. Adsorbent devices 508 (in FIG. 5A), 510 (in FIG. 5B), and 512 (in FIG. 5C) have an inlet port to which the ultrafiltrate tubing which carries the ultrafiltrate from hemofilter 108 (in FIGS. 1A and 1B) and hemofilter 208 (in FIG. 2) will be attached to provide ultrafiltrate flow to adsorbent devices 508, 510, or 512. Ultrafiltrate flow through adsorbent device 508 (in FIG. 5A), 510 (in FIG. 5B), and 512 (in FIG. 5C), perfuses the adsorbent materials allowing for adsorption of IM, and flows out of the adsorbent device through an outlet port.

Referring to FIG. 5C, where a multiple chamber configuration is used for adsorptive device 512, the chambers will be separated by a screen or other porous barrier which retains the adsorbent materials or combinations of adsorbent materials in their separate compartments and allows free flow of ultrafiltrate through adsorptive device 512. An alternative embodiment utilizes separate, exchangeable modules each containing an adsorbent material or adsorbent materials. A module or a combination of modules may be inserted into the adsorbent device to provide for the adsorption of different types of IM as the condition of the mammal may require. Although not shown, adsorbent device 108 (in FIGS. 1A and 1B) and adsorptive device 208 (in FIG. 2) can be incorporated into or combine with hemofilter 102 (in FIGS. 1A and 1B) and hemofilter 202 (in FIG. 2), respectively. In this embodiment ultrafiltrate formed at the hemofilter membrane will pass into the hemofilter jacket, the hemofilter jacket will incorporate the adsorptive materials in one or more chambers and ultrafiltrate will flow through the adsorbent materials. Ultrafiltrate will transfer from the combined hemofilter/adsorbent device through an outlet port to post adsorbent ultrafiltrate tubing.

The amount of blood continuously pumped will be operator determined and depend on the condition of mammal 100 (in FIGS. 1A and 1B) and mammal 200 (in FIG. 2) and the needs of effective HF. The amount of blood continuously removed must be determined on a case by case basis. The flow rate, the amount of blood removed and the duration of the HF therapy are determined by the weight, the age and the nature and severity of illness of mammal. Typically, blood flow rates range from 100 to 200 ml/minute. The rate of ultrafiltration depends on the nature and severity of illness and is indexed to body weight, total body water and/or clinical indices of disease management (e.g., pulmonary function, cardiovascular status, etc.). Typically, total ultrafiltrate flow rate is 1 to 9 liters/hour of which from 0 to 2 liters/hour may be discarded. The discard rate will be determined by the fluid balance requirements of the mammal. The amount of ultrafiltrate discarded will be determined by operator as operator judges the needs of mammal 100 and mammal 200 for fluid removal. All ultrafiltrate not discarded is returned to mammal 100 (in FIGS. 1A and 1B) and mammal 200 (in FIG. 2).

With respect to the tubing used in preferred embodiments for tubing, the composition of the material making up the blood pump tubing, ultrafiltrate tubing, etc., is preferably of a biocompatible material, such as polyvinylchloride, but not limited to this material. The tubing will be flexible and have outside diameters complementary to the appropriate hemofilter connections, adsorptive device connections, joints, stop cocks, or pump heads.

Specifically, with respect to the tubing in FIG. 1A, first tubing 101 transfers blood from mammal 100 to blood pump 104; second tubing 103 transfers blood from blood pump 104 to hemofilter 102; third tubing 105 transfers the filtered blood filtered by hemofilter 102 to second three-way joint 125; fourth tubing 107 transfers the filtered blood along with the post adsorption ultrafiltrate to mammal 100; fifth tubing 112 transfers the ultrafiltrate to adsorptive device 108; sixth tubing 123 transfers the post adsorption ultrafiltrate to three-way stop cock or second three-way joint 110; seventh tubing 131 transfers post adsorption ultrafiltrate to first ultrafiltrate pump 106a; eighth tubing 129 transfers post adsorption ultrafiltrate from first ultrafiltrate pump 106a to second three-way joint 125 joining fourth tubing 107 which transfers filtered blood along with the post adsorption ultrafiltrate to the mammal; ninth tubing 127 transfers post adsorption ultrafiltrate to second ultrafiltrate pump 106b; and tenth tubing 121 transfers post adsorption ultrafiltrate from second ultra filtrate pump 106b to waste reservoir 119. First ultrafiltrate pump 106a and associated tubing implement steps 311 and 312 in FIG. 3A; second ultrafiltrate pump 106b, waste reservoir 119, and associated tubing implement steps 309 and 310 in FIG. 3A.

With respect to the tubing in FIG. 1B, first tubing 101 transfers blood from mammal 100 to blood pump 104; second tubing 103 transfers blood from blood pump 104 to hemofilter 102; third tubing 105 transfers the filtered blood filtered by hemofilter 102 to second three-way joint 125; fourth tubing 107 transfers the filtered blood along with the post adsorption ultrafiltrate to mammal 100; fifth tubing 112 transfers the ultrafiltrate to adsorptive device 108; sixth tubing 123 transfers the post adsorption ultrafiltrate or ultrafiltrate stream 115 to single ultrafiltrate pump 106; seventh tubing 131 transfers post adsorption ultrafiltrate from ultrafiltrate pump 106 to three-way stop cock or first three-way joint 110; eighth tubing 129 transfers post adsorption ultrafiltrate from three-way stop cock or first three-way joint 110 to second three-way joint 125 joining fourth tubing 107 which transfers filtered blood along with the post adsorption ultrafiltrate to mammal 100; and ninth tubing 127 transfers post adsorption ultrafiltrate from three-way stop cock or first three-way joint 110 to waste reservoir 119. Single ultrafiltrate pump 106 and associated tubing implement step 351 in FIG. 3B; waste reservoir 119 and associated tubing implement step 310 in FIG. 3B. Second three-way joint 125 and associated tubing implement step 312 in FIG. 3B.

With respect to the tubing in FIG. 2, first tubing 201 transfers blood from mammal 200 to blood pump 204; second tubing 203 transfers blood from blood pump 204 to hemofilter 202; third tubing 205 transfers the filtered blood filtered by hemofilter 202 to second three-way joint 225; fourth tubing 207 transfers the filtered blood along with the post adsorption ultrafiltrate to mammal 200; fifth tubing 212 transfers the ultrafiltrate 211 to three-way stop cock or first three-way joint 210; sixth tubing 215 transfers the ultrafiltrate from three-way stop cock or first three-way joint 210 to adsorptive device 208; seventh tubing 229 transfers the post adsorption ultrafiltrate or ultrafiltrate stream 216 to first ultrafiltrate pump 206a; eighth tubing 223 transfers post adsorption ultrafiltrate from first ultrafiltrate pump 206a to second three-way joint 225 joining fourth tubing 207 which transfers filtered blood along with the post adsorption ultrafiltrate to mammal 200; ninth tubing 225 transfers ultrafiltrate from three-way stop cock or first three-way joint 210 to second ultrafiltrate pump 206b; and tenth tubing 233 transfers ultrafiltrate from second ultrafiltrate pump 206b to waste reservoir 219. First ultrafiltrate pump 206a and associated tubing implement steps 411 and 412 in FIG. 4; second ultrafiltrate pump 206b and waste reservoir 219 and associated tubing implement steps 409 and 410 in FIG. 4.

Further Modifications and Variations

Although the invention has been described with reference to a specific embodiment, this description is not meant to be construed in a limiting sense. The example embodiments shown and described above are only intended as an example. Other applications of the preferred embodiments may be found as well. Various modifications of the disclosed embodiment as well as alternate embodiments of the invention will become apparent to persons skilled in the art upon reference to the description of the invention. For instance, structural modification could include the integration of hemofilter 102 in FIGS. 1A and 1B and hemofilter 202 in FIG. 2 with adsorptive device 108 (in FIGS. 1A and 1B) and adsorptive device 208 (in FIG. 2), both of which have one or more chambers containing adsorbent material of one or more types, with elimination of the additional tubing. In this embodiment ultrafiltrate formed in jacket of hemofilter 102 (in FIGS. 1A and 1B) and hemofilter 202 (in FIG. 2) would be presented directly to adsorbent material contained with in hemofilter jacket or in a chamber or chambers directly contiguous with hemofilter jacket. The chamber containing ultrafiltrate would be drained by ultrafiltrate line. Ultrafiltrate would be continuously pumped and apportioned for discard or returned to mammal 100 (in FIGS. 1A and 1B) and mammal 200 (in FIG. 2). In addition, it is possible to modify the configuration of ultrafiltrate lines to provide for infusion of ultrafiltrate into mammal 100 (in FIGS. 1A and 1B) or mammal 200 (in FIG. 2) via a vascular cannula in a blood vessel and separate from the hemofiltration circuit. Furthermore, note the ultrafiltrate return pump and the ultrafiltrate discard pump in the preferred embodiment shown and discussed above may be combined into a single two head ultrafiltrate pump system. Also, note while the ultrafiltrate return pump and the ultrafiltrate discard pump are shown in the figures as two separate pumps, it is within the scope of the invention to combine two pumps into a single pump, and thus, the separate pumps may be interpreted as two parts of a single pump.

Modifications of adsorbent device will be determined by the inflammatory mediator related disease (IMRD) to be treated and the phase of the disease. Various regions of the IM network are dominant at different phases of an IMRD and different IMRD exhibit different patterns of IM networking. Thus a different adsorbent material or materials, or different groupings of adsorbent materials will be needed for different IMRD's in their different phases. Thus different adsorbent devices will be developed as more is learned of IMRD's and their phases. Adsorbent devices may contain a fixed adsorbent material or a fixed combination of adsorbent materials. Alternatively, an adsorbent device may be configured with different, interchangeable modules of adsorbent materials to be adapted to the changing dominance of the IM network. The modules may consist of one or more chambers containing adsorbent material of one or more types. The adsorbent device may be designed to accept modules of adsorbent materials inserted in place as dictated by patient need and operator assessment.

Different configurations of adsorbent materials will be used. Adsorbent materials exhibit chemical characteristics which determine what physical form will provide the greatest stability in flowing ultrafiltrate. Adsorbent material must remain irreversibly bound to its supporting matrix, or in the case of beads (e.g. polysulfone, polyacrylonitrile, etc.) or particulates (e.g. charcoal) inescapably contained in mesh or other containment device. Adsorbent material, matrix, and containment material can not be allowed to dissolve, dissociate or fragment into the ultrafiltrate to be infused into the mammal. Adsorbent material, matrix, and containment material must be configured to provide physical durability, and adequate porosity and configuration for optimal presentation of adsorbent material to flowing ultrafiltrate. Some configurations of matrix are shown in FIGS. 5A, 5B, and 5C. Adsorbent devices of one or more chambers containing adsorbent material of one or more types could be used in series, in which ultrafiltrate flows from the first to subsequent adsorbent devices. The sequence, number and type of adsorbent devices would be determined by operator to meet the needs of mammal. Alternatively, the ultrafiltrate stream could be divided by a manifold with distribution of ultrafiltrate to adsorbent devices arranged in a parallel configuration, with each line from each adsorbent device either returned to a manifold and reunited into a single ultrafiltrate line, or each line individually apportioned for return to mammal and discard.

Thus, even though numerous characteristics and advantages of the present inventions have been set forth in the foregoing description, together with details of the structure and function of the inventions, the disclosure is illustrative only, and changes may be made in the detail, especially in matters of shape, size and arrangement of the parts within the principles of the inventions to the full extent indicated by the broad general meaning of the terms used in the attached claims. Accordingly, it should be understood that the modifications and variations suggested above and below are not intended to be exhaustive. These examples help show the scope of the inventive concepts, which are covered in the appended claims. The appended claims are intended to cover these modifications and alternate embodiments.

In short, the description and drawings of the specific examples above are not intended to point out what an infringement of this patent would be, but are to provide at least one explanation of how to make and use the inventions contained herein. The limits of the inventions and the bounds of the patent protection are measured by and defined in the following claims.

What is claimed is:

1. A method for treating inflammatory mediator related diseases including sepsis, septic shock, systemic inflammatory response syndrome, multiple organ system dysfunction syndrome, and multiple organ system failure in a mammal comprising:

pumping blood from the mammal using a blood pump;

transferring the blood from the blood pump to a hemofilter;

removing an ultrafiltrate from the blood using the hemofilter to create a filtered blood stream and an ultrafiltrate stream;

transferring the ultrafiltrate stream from the hemofilter to an adsorptive device containing at least one fixed adsorbent material;

selectively removing at least one inflammatory mediator which causes an inflammatory mediator related disease from the ultrafiltrate stream using the adsorbent material to create a post adsorption ultrafiltrate stream;

combining at least a portion of the post adsorption ultrafiltrate stream with the filtered blood stream and returning the combined post adsorption ultrafiltrate stream and the filtered blood stream to the mammal; and transferring a portion of the post adsorption ultrafiltrate stream which is not returned to the mammal to a waste reservoir.

2. The method of claim 1 further comprising transferring the post adsorption ultrafiltrate stream from the adsorptive device using an ultrafiltrate pump.

3. The method of claim 1 further comprising:

transferring the post adsorption ultrafiltrate stream from the adsorptive device using a first ultrafiltrate pump; and transferring a portion of the post adsorption ultrafiltrate stream which is not returned to the mammal to the waste reservoir using a second ultrafiltrate pump.

4. A hemofiltration system to treat an inflammatory mediator related disease in a mammal, comprising:

a hemofilter operable to remove ultrafiltrate from a blood stream extracted from the mammal and to create a filtered blood stream and an ultrafiltrate stream;

the hemofilter having a molecular weight exclusion limit equal to or greater than approximately 69,000 Daltons;

an adsorptive device containing at least one adsorbent material operable to receive the ultrafiltrate stream from the hemofilter and to remove a wide range of inflammatory mediators therefrom to create a post adsorption ultrafiltrate stream;

the adsorbent material selected from a group consisting of coated materials, uncoated materials, a matrix of rods, a matrix configured for convenient presentation of ultrafiltrate to adsorbent material, beads, and particulates and any combination thereof; and tubing for use in combining the post adsorption ultrafiltrate stream with the filtered blood stream and returning the combined stream to the mammal.

5. The hemofiltration system of claim 4, wherein the adsorbent material is comprised of adsorbent resins selected from a group consisting of immobilized polymyxin B, polystyrene-derivative fibers, cation exchange resins, neutral exchange resins, anion exchange resins, cellulose materials, polysulfone, polyacrylonitrile, polymethylmethacrylate, polyvinyl-alcohol, polyamide, polycarbonate, cellulose derivatives, specific antibody coated materials, specific antagonist coated materials, and any combination thereof.

6. The hemofiltration system of claim 4, wherein the ultrafiltrate stream comprises plasma water, electrolytes, blood peptides and proteins.

7. The hemofiltration system of claim 4, wherein the hemofilter comprises a material selected from the group of polysulfone, polyacrylonitrile, polymethylmethacrylate, polyvinyl-alcohol, polyamide, polycarbonate, and cellulose derivatives, and the jacket comprises polycarbonate.

8. The process of claim 4, wherein the adsorbent material is selected from a group consisting of activated charcoal, uncharged resins, charged resins, silica, immobilized polymyxin B, anion exchange resin, cation exchange resin, neutral exchange resin, polysulfone, polyacrylonitrile, polymethyl-methacrylate, polyvinyl-alcohol, polyamide, polycarbonate, cellulose derivatives, immobilized monoclonal antibodies, immobilized IM receptors, immobilized specific antagonists, and any combination thereof.

9. A method for treating inflammatory mediator related disease including sepsis, septic shock, and inflammatory mediator-related diseases such as systemic inflammatory response syndrome, multiple organ system dysfunction syndrome, and multiple organ system failure in a mammal comprising;
    pumping blood from the mammal using a blood pump;
    transferring the blood from the blood pump to a hemofilter;
    removing an ultrafiltrate from the blood using the hemofilter to create a filtered blood stream and an ultrafiltrate stream;
    transferring the ultrafiltrate stream from the hemofilter to an adsorptive device containing at least one fixed adsorbent material;
    selectively removing at least one inflammatory mediator which causes an inflammatory mediator related disease from the ultrafiltrate stream using the adsorbent material to create a post adsorption ultrafiltrate stream;
    combining a portion of the post adsorption ultrafiltrate stream with the filtered blood stream and returning the combined post adsorption ultrafiltrate stream and the filtered blood stream to the mammal; and
    transferring a portion of the post adsorption ultrafiltrate stream which is not returned to the mammal to a waste reservoir.

10. The method of claim 9 further comprising transferring the post adsorption ultrafiltrate stream from the adsorptive device using an ultrafiltrate pump.

11. The method of claim 9 further comprising:
    transferring the post adsorption ultrafiltrate stream from the adsorptive device using a first ultrafiltrate pump; and
    transferring a portion of the post adsorption ultrafiltrate stream which is not returned to the mammal to the waste reservoir using a second ultrafiltrate pump.

12. A hemofiltration system to treat an inflammatory mediator related disease including sepsis and septic shock in a mammal, comprising:
    a hemofilter operable to remove ultrafiltrate from a blood stream extracted from the mammal and to create a filtered blood stream and an ultrafiltrate stream;
    the hemofilter having a molecular weight exclusion limit selected to be larger than a molecular size of the blood peptides and proteins;
    an adsorptive device containing at least one adsorbent material operable to receive the ultrafiltrate stream from the hemofilter and to remove at least one inflammatory mediator therefrom to create a post adsorption ultrafiltrate stream;
    the adsorbent material selected from a group consisting of coated materials, uncoated materials, a matrix of rods, a matrix configured for convenient presentation of ultrafiltrate to adsorbent material, beads, and particulates and any combination thereof; and
    means for selectively combining the post adsorption ultrafiltrate stream with the filtered blood stream and returning the combined stream to the mammal.

13. The hemofiltration system of claim 12, wherein the adsorbent material is comprised of adsorbent resins selected from a group consisting of immobilized polymyxin B, polystyrene-derivative fibers, cation exchange resins, neutral exchange resins, anion exchange resins, cellulose materials, polysulfone, polyacrylonitrile, polymethylmethacrylate, polyvinyl-alcohol, polyamide, polycarbonate, cellulose derivatives, specific antibody coated materials, specific antagonist coated materials, and any combination thereof.

14. The hemofiltration system of claim 12, wherein the ultrafiltrate stream comprises plasma water, electrolytes, blood peptides and proteins.

15. The hemofiltration system of claim 12, wherein the hemofilter comprises a material selected from the group of polysulfone, polyacrylonitrile, polymethylmethacrylate, polyvinyl-alcohol, polyamide, polycarbonate, and cellulose derivatives, and the jacket comprises polycarbonate.

16. The process of claim 12, wherein the adsorbent material is selected from a group consisting of activated charcoal, uncharged resins, charged resins, silica, immobilized polymyxin B, anion exchange resin, cation exchange resin, neutral exchange resin, polysulfone, polyacrylonitrile, polymethyl-methacrylate, polyvinyl-alcohol, polyamide, polycarbonate, cellulose derivatives, immobilized monoclonal antibodies, immobilized IM receptors, immobilized specific antagonists, and any combination thereof.

17. A hemofiltration system to treat an inflammatory mediator related disease including sepsis and septic shock in a mammal comprising:
    a blood pump to pump blood from the mammal;
    a first tubing to transfer the blood from the mammal to the blood pump;
    a hemofilter to receive the blood removed from the mammal, the hemofilter operable to remove an ultrafiltrate from the blood to create a filtered blood stream and an ultrafiltrate stream;
    a second tubing to transfer the blood from the blood pump to the hemofilter;
    a third tubing to transfer the filtered blood stream from the hemofilter to the mammal;
    an adsorptive device containing at least one fixed adsorbent material to receive the ultrafiltrate stream from the hemofilter;
    the adsorbent material operable to remove inflammatory mediators that cause the inflammatory mediator related disease from the ultrafiltrate stream to create a post adsorption ultrafiltrate stream;
    a fourth tubing to transfer the ultrafiltrate stream from the hemofilter to the adsorptive device;

means for selectively combining the post adsorption ultrafiltrate stream with the filtered blood stream and returning the combined stream of post adsorption ultrafiltrate and the filtered blood to the mammal including a fifth tubing to transfer the post adsorption ultrafiltrate stream from the adsorptive device;

a sixth tubing to transfer the combined stream of post adsorption ultrafiltrate and the filtered blood to the mammal; and an seventh tubing to transfer any of the post adsorption ultrafiltrate which is not combined with the filtered blood to a waste reservoir.

18. The hemofiltration system of claim 17, wherein the adsorbent material is selected from a group consisting of activated charcoal, uncharged resins, charged resins, silica, immobilized polymyxin B, anion exchange resin, cation exchange resin, neutral exchange resin, polysulfone, polyacrylonitrile, polymethylmethacrylate, polyvinyl-alcohol, polyamide, polycarbonate, cellulose derivatives, immobilized monoclonal antibodies, immobilized IM receptors, immobilized specific antagonists, and any combination thereof.

19. The hemofiltration system of claim 17, wherein the adsorptive device prevents dissolution and fragmentation of the adsorbent material.

20. The hemofiltration system of claim 17, wherein the adsorbent material is comprised of adsorbent resins selected from a group consisting of immobilized polymyxin B polystyrene-derivative fibers, anion exchange resins, cation exchange resins, neutral exchange resins, cellulose materials, polysulfone, polyacrylonitrile, polymethylmethacrylate, polyvinyl-alcohol, polyamide, polycarbonate, cellulose derivatives, specific antagonist coated materials and specific antibody coated materials.

21. The hemofiltration system of claim 17, wherein the ultrafiltrate comprising plasma water, electrolytes, blood peptides, proteins, carbohydrates, and lipids.

22. The hemofiltration system of claim 17 wherein the hemofilter comprises a molecular weight exclusion limit selected such that blood peptides and proteins are filtered therethrough.

23. A hemofiltration system to treat an inflammatory mediator related disease including sepsis and septic shock in a mammal, comprising:

a hemofilter to receive blood removed from the mammal, the hemofilter operable to remove an ultrafiltrate from the blood removed from the mammal to create filtered blood;

an adsorptive device containing at least one fixed adsorbent material to receive the ultrafiltrate removed from the blood removed from the mammal, the adsorbent material operable to remove inflammatory mediators that cause the inflammatory mediator related disease from the ultrafiltrate to create post adsorption ultrafiltrate;

the adsorbent material selected from a group consisting of coated materials, uncoated materials, a matrix of rods, a matrix configured for convenient and effective presentation of ultrafiltrate to adsorbent materials, beads, and particulates and any combination thereof;

means for combining at least a portion of the post adsorption ultrafiltrate with at least a portion of the filtered blood and returning the combined post adsorption ultrafiltrate and the filtered blood to the mammal; and means for discarding any portion of the post adsorption ultrafiltrate and any portion of the filtered blood which is not returned to the mammal.

24. A hemofiltration system to treat an inflammatory mediator related disease including sepsis and septic shock in a mammal comprising:

a blood pump to pump a blood stream from the mammal;

a hemofilter operable to remove ultrafiltrate from the blood stream extracted from the mammal and to create a filtered blood stream and an ultrafiltrate stream;

an adsorptive device containing at least one adsorbent material operable to receive the ultrafiltrate stream from the hemofilter and to remove inflammatory mediators therefrom to create a post adsorption ultrafiltrate stream;

means for selectively combining the post adsorption ultrafiltrate stream with the filtered blood stream along with returning the combined stream to the mammal to treat the inflammatory mediator related disease;

a first tubing to transfer the combined stream to the mammal;

a second tubing to transfer any of the post adsorption ultrafiltrate stream which is not returned to the mammal to a waste reservoir;

at least a first ultrafiltrate pump operably coupled with the adsorptive device to assist with transferring the post adsorptive ultrafiltrate stream from the adsorptive device; and at least a second ultrafiltrate waste pump operably coupled with the second tubing to assist with transferring any of the post adsorption ultrafiltrate stream which is not returned to the mammal to the waste reservoir.

25. The system of claim 24, wherein the adsorbent material is comprised of resins selected from a group consisting of immobilized polymyxin B, polystyrene-derivative fibers, charged exchange resins, neutral exchange resins; polysulfone, polyacrylonitrile, polymethylmethacrylate, polyvinyl-alcohol, polyamide, polycarbonate, and cellulose derivatives, specific antagonist coated materials, and specific antibody coated materials.

26. The system of claim 24, using a hemofilter to remove the ultrafiltrate from the blood stream to create the filtered blood stream and the ultrafiltrate stream comprising plasma water, electrolytes blood peptides and proteins.

27. The system of claim 24, wherein the hemofilter comprises a membrane having at least one pore with a pore size selected to be larger than a molecular size of the blood peptides and proteins.

28. The system of claim 24, wherein the hemofilter comprises a material selected from the group of polysulfone, polyacrylonitrile, polymethylmethacrylate, polyvinyl-alcohol, polyamide, polycarbonate, and cellulose derivatives, and the jacket comprises polycarbonate.

29. A method for treating inflammatory mediator related diseases including sepsis, septic shock, systemic inflammatory response syndrome, multiple organ system dysfunction syndrome, and multiple organ system failure in a mammal comprising;

pumping blood from the mammal using a blood pump;

transferring the blood from the blood pump to a hemofilter;

removing an ultrafiltrate from the blood using the hemofilter to create a filtered blood stream and an ultrafiltrate stream;

transferring the ultrafiltrate stream from the hemofilter to an adsorptive device containing at least one fixed adsorbent material;

selectively removing at least one inflammatory mediator which causes an inflammatory mediator related disease from the ultrafiltrate stream using the adsorbent material to create a post adsorption ultrafiltrate stream;

combining at least a portion of the post adsorption ultrafiltrate stream with the filtered blood stream and returning the combined post adsorption ultrafiltrate stream and the filtered blood stream to the mammal;

transferring the post adsorption ultrafiltrate stream from the adsorptive device using a first ultrafiltrate pump; and transferring a portion of the post adsorption ultrafiltrate stream which is not returned to the mammal to the waste reservoir using a second ultrafiltrate pump.

30. A hemofiltration system to treat an inflammatory mediator related disease in a mammal, comprising:

a hemofilter operable to remove ultrafiltrate from a blood stream extracted from the mammal and to create a filtered blood stream and an ultrafiltrate stream;

the hemofilter having a molecular weight exclusion limit equal to or greater than approximately 69,000 Daltons;

an adsorptive device containing at least one adsorbent material operable to receive the ultrafiltrate stream from the hemofilter and to remove a wide range of inflammatory mediators therefrom to create a post adsorption ultrafiltrate stream; the adsorbent material selected from a group consisting of coated materials, uncoated materials, a matrix of rods, a matrix configured for convenient presentation of ultrafiltrate to adsorbent material, beads, and particulates and any combination thereof; and tubing for use in combining the post adsorption ultrafiltrate stream with the filtered blood stream and returning the combined stream to the mammal;

a first ultrafiltrate pump to transfer the post adsorption ultrafiltrate stream from the adsorptive device; and a second ultrafiltrate pump to transfer a portion of the post adsorption ultrafiltrate stream which is not returned to the mammal to the waste reservoir using a second unltrafiltrate pump.

31. The hemofiltration system of claim 30 wherein the adsorbent material is comprised of adsorbent resins selected from a group consisting of immobilized polymyxin B, polystyrene-derivative fibers, cation exchange resins, neutral exchange resins, anion exchange resins, cellulose materials, polysulfone, polyacrylonitrile, polymethylmethacrylate, polyvinyl-alcohol, polyamide, polycarbonate, cellulose derivatives, specific antibody coated materials, specific antagonist coated materials, and any combination thereof.

32. A method for treating inflammatory mediator related disease including sepsis, septic shock, and inflammatory mediator-related diseases such as systemic inflammatory response syndrome, multiple organ system dysfunction syndrome, and multiple organ system failure in a mammal comprising;

pumping blood from the mammal using a blood pump;

transferring the blood from the blood pump to a hemofilter;

removing an ultrafiltrate from the blood using the hemofilter to create a filtered blood stream and an ultrafiltrate stream;

transferring the ultrafiltrate stream from the hemofilter to an adsorptive device containing at least one fixed adsorbent material;

selectively removing at least one inflammatory mediator which causes an inflammatory mediator related disease from the ultrafiltrate stream using the adsorbent material to create a post adsorption ultrafiltrate stream;

combining a portion of the post adsorption ultrafiltrate stream with the filtered blood stream and returning the combined post adsorption ultrafiltrate stream and the filtered blood stream to the mammal; and transferring all of the post adsorption ultrafiltrate stream which is not returned to the mammal to a waste reservoir.

33. A method for treating inflammatory mediator related diseases including sepsis, septic shock, systemic inflammatory response syndrome, multiple organ system dysfunction syndrome, and multiple organ system failure in a mammal comprising:

pumping blood from the mammal using a blood pump;

transferring the blood from the blood pump to a hemofilter;

removing an ultrafiltrate from the blood using the hemofilter to create a filtered blood stream and an ultrafiltrate stream;

transferring the ultrafiltrate stream from the hemofilter to an adsorptive device containing at least one fixed adsorbent material;

selectively removing at least one inflammatory mediator which causes an inflammatory mediator related disease from the ultrafiltrate stream using the adsorbent material to create a post adsorption ultrafitrate stream; and combining at least a portion of the post adsorption ultrafiltrate stream with the filtered blood stream and returning the combined post adsorption ultrafiltrate stream and the filtered blood stream to the mammal.

34. A method for treating inflammatory meidator related disease including sepsis, septic shock, systemic inflammatory response syndrome, multiple organ system dysfunction syndrome, and multiple organ system failure in a mammal comprising:

pumping blood from the mammal using a blood pump;

transferring the blood from the blood pump to a hemofilter;

removing an ultrafiltrate from the blood using the hemofilter to create a filtered blood stream and an ultrafiltrate stream;

transferring the ultrafiltrate stream from the hemofilter to an adsorptive device containing at least one fixed adsorbent material;

selectively removing at least one inflammatory mediator which causes an inflammatory mediator related disease from the ultrafiltrate stream using the adsorbent material to create a p ost adsorption ultrafiltrate stream; and transferring at least a portion of the post adsorption ultrafiltrate stream to a waste reservoir.

* * * * *